(12) United States Patent
Chu et al.

(10) Patent No.: US 8,139,840 B1
(45) Date of Patent: Mar. 20, 2012

(54) INSPECTION SYSTEM AND METHOD FOR HIGH-SPEED SERIAL DATA TRANSFER

(75) Inventors: Yunxian Chu, Fremont, CA (US); Alexander Slobodov, San Jose, CA (US)

(73) Assignee: KLA-Tencor Corporation, San Jose, CA (US)

( * ) Notice: Subject to any disclaimer, the term of this patent is extended or adjusted under 35 U.S.C. 154(b) by 991 days.

(21) Appl. No.: 12/100,500

(22) Filed: Apr. 10, 2008

(51) Int. Cl.
*G06K 9/00* (2006.01)

(52) U.S. Cl. .................................................. 382/141

(58) Field of Classification Search .............. 382/141, 382/144, 145
See application file for complete search history.

(56) References Cited

U.S. PATENT DOCUMENTS

| | | | |
|---|---|---|---|
| 5,528,587 | A | 6/1996 | Galand et al. |
| 6,115,747 | A | 9/2000 | Billings et al. |
| 6,580,853 | B2 | 6/2003 | Harrison et al. |
| 6,952,213 | B2 | 10/2005 | Ebihara |
| 7,003,585 | B2 | 2/2006 | Phong et al. |
| 7,106,895 | B1 * | 9/2006 | Goldberg et al. ............ 382/144 |
| 7,130,054 | B2 | 10/2006 | Ostrovsky et al. |
| 7,149,642 | B1 | 12/2006 | Bhaskar et al. |
| 7,170,964 | B2 | 1/2007 | Kocaman et al. |
| 7,184,511 | B2 | 2/2007 | Younis et al. |
| 7,215,808 | B2 | 5/2007 | Miller |
| 7,724,939 | B2 * | 5/2010 | Goldberg et al. ............ 382/141 |
| 2003/0016697 | A1 | 1/2003 | Jordan |
| 2003/0031133 | A1 | 2/2003 | Momtaz |
| 2005/0100058 | A1 | 5/2005 | Goder |
| 2006/0050726 | A1 | 3/2006 | Ahmed et al. |
| 2006/0067387 | A1 | 3/2006 | Ahmed et al. |
| 2006/0114811 | A1 | 6/2006 | Ahmed et al. |
| 2006/0156161 | A1 | 7/2006 | Warner et al. |
| 2006/0167947 | A1 | 7/2006 | Dunkle |
| 2006/0215782 | A1 | 9/2006 | Ahmed et al. |
| 2006/0269119 | A1 * | 11/2006 | Goldberg et al. ............ 382/144 |
| 2007/0016034 | A1 | 1/2007 | Donaldson |
| 2007/0023658 | A1 | 2/2007 | Nozoe et al. |
| 2007/0024869 | A1 | 2/2007 | Ostrovsky et al. |
| 2007/0036421 | A1 | 2/2007 | Toba et al. |
| 2007/0067481 | A1 | 3/2007 | Sharma et al. |
| 2007/0076123 | A1 | 4/2007 | Ogilvie |
| 2007/0086479 | A1 | 4/2007 | Ling et al. |
| 2007/0119518 | A1 | 5/2007 | Carman et al. |
| 2007/0165770 | A1 | 7/2007 | Vogtmeier |

* cited by examiner

*Primary Examiner* — Patrick J Connolly
(74) *Attorney, Agent, or Firm* — Kevin L. Daffer; Daffer McDaniel, LLP

(57) ABSTRACT

An inspection system and method for serial high-speed image data transfer is provided herein. According to one embodiment, the method may include receiving multiple channels of image data at an input data rate and buffering the image data at the input data rate until the buffered data reaches a predetermined size. Once the predetermined size has been reached, the method may include packing the buffered data, encoding the data packet, serializing the encoded data packet and converting the encoded data packet into an optical signal. In some cases, the image data may be packed along with a data header containing information about the system. Once converted, each optical signal (i.e., representing one data packet) may be transmitted serially over one or more fibre channels to a processing node of the inspection system. In most cases, the data is packed, encoded, serialized and transmitted to the processing node at a data rate much higher than the input data rate. The processing node analyzes the optical signal to detect defects on a specimen under inspection.

25 Claims, 6 Drawing Sheets

INSPECTION SYSTEM AND METHOD FOR HIGH-SPEED SERIAL DATA TRANSFER

BACKGROUND OF THE INVENTION

1. Field of the Invention

This invention relates to semiconductor inspection and, more particularly, to inspection systems and methods for transferring and processing inspection images.

2. Description of the Related Art

The following descriptions and examples are given as background only.

Semiconductor devices, such as logic, memory and other integrated circuit devices, are fabricated by processing a specimen (such as a semiconductor wafer) to form various features and multiple levels of the semiconductor device. Lithography is one example of a semiconductor fabrication process that may be used to transfer a pattern to a resist arranged on a semiconductor wafer. Additional examples of semiconductor fabrication processes include, but are not limited to, chemical-mechanical polishing, etch, deposition, and ion implantation. Multiple semiconductor devices can be fabricated in an arrangement on a semiconductor wafer and then separated into individual semiconductor devices.

Inspection methods are used at various stages of the manufacturing process to detect defects on the wafers. Inspection has always played an important role in semiconductor fabrication. However, inspection has become increasingly important to the successful manufacture of acceptable semiconductor devices as the dimensions of the devices continue to decrease. For instance, detecting defects of decreasing size has become increasingly necessary, since even relatively small defects may cause unwanted aberrations in the semiconductor device, sometimes causing the device to fail.

Many different types of inspection tools have been developed for the inspection of semiconductor wafers, including optical and E-beam systems. Most optical inspection tools can be characterized into bright-field (BF) and dark-field (DF) systems. Bright-field systems direct light to a wafer at a particular angle and measure the amount of light reflected from the surface of the wafer at a similar angle. Bright-field systems typically use high-resolution imaging optics, and the inspection of the wafer is performed in such a manner that the pixel size is very small. The small pixel size takes advantage of the high-resolution imaging optics and the large amount of reflected light to generate inspection images with a great amount of detail. As such, BF systems are typically used for imaging patterns (e.g., memory cells or circuit features) formed on the wafer.

On the other hand, dark-field systems detect the amount of light, which is scattered from the surface of a wafer when an incident beam is supplied to the wafer at a normal or oblique angle. In the case of dark-field inspection, smooth surfaces lead to almost no collection signal, while surfaces with protruding features (such as patterned features or defects) tend to scatter much more strongly (sometimes up to six orders of magnitude or more). As such, DF systems are typically used for detecting defects or particles that may be present on a patterned or unpatterned wafer. Darkfield illumination provides a larger pixel-to-defect ratio than bright-field illumination, permitting faster inspections for a given defect size and pixel rate. Darkfield imaging also permits Fourier filtering to enhance signal to noise ratios. Some inspection tools reap the benefits of both systems by combining bright-field and dark-field techniques within the same tool.

Regardless of the type of inspection system used, the inspection images must be analyzed to determine whether a wafer is acceptable. In some inspection systems, one or more sensor arrays may be used to detect light propagating from the wafer in response to BF or DF illumination light. Charge coupled device (CCD) and time delay integration (TDI) cameras are two examples of sensor arrays commonly used for this purpose. As illumination light is scanned across the surface of the wafer, the sensor arrays convert the detected light into electrical signals, which are typically transferred in parallel, via multiple data channels, to one or more processing nodes of the inspection system. The processing nodes may utilize a variety of different algorithms to analyze the electrical signals (i.e., the image data) for defect detection.

The image data obtained by the sensor array is usually analyzed by a number of processors connected together in series, or in parallel. In the serial configuration, the parallel image data from the sensor array is supplied to a first processor. After serialization, the first processor performs one step of the analysis and the resultant data is supplied to the next processor in the serial chain for the next step in the analysis algorithm. The image data may be fed into any number of serially-coupled processors, with each processor in the chain performing some small portion of the total analysis algorithm. In the parallel configuration, inspection speed is improved by supplying the parallel image data to all processors at the same time. Each processor may be coupled for receiving the entire inspection image, or only a portion of the image data. As such, the parallel processors may perform separate analysis algorithms, or different steps of the same analysis program.

Regardless of the processing configuration used, conventional inspection systems typically fail to maximize inspection speed, reliability and scalability. As noted above, most inspection systems transfer image data to the processing nodes in parallel. Such data transfer methods suffer from limited data transfer rates, signal integrity problems and require numerous wires and connectors, which are bulky and unreliable. In addition, many inspection systems locate processing nodes inside the inspection tool, itself. As set forth below, internal processing nodes are often limited in space, power, processing capabilities and scalability.

FIG. 7 illustrates one embodiment of a conventional inspection tool 600 including illumination subsystem 610 for providing illumination light to specimen 620, collection subsystem 630 for collecting light propagating from the specimen and detection subsystem 640 for detecting light collected by the collection subsystem. The image data from detection subsystem 640 is transferred in parallel, via multiple channels (e.g., channels CH0-CHN), to a processing subsystem within the inspection tool. In one embodiment, the processing subsystem may include analog-to-digital converter (ADC) 650 for digitizing the image data and interface card 660 for serializing the image data. A number of parallel buses (e.g., buses B0-BN) are used to couple the ADC to the interface card. The buses typically use a relatively high speed bus protocol, such as low voltage differential signaling (LVDS) or HyperTransport, to transfer the parallel image data between the ADC and interface card.

As shown in FIG. 7, digital signal processor (DSP) boards 670 are included within inspection tool 600 for processing the image data to detect defects. The DSP boards may include any number of processors coupled together on a common backplane. The individual processors may be coupled in series or in parallel, as discussed above. The inspection results from the DSP boards may be supplied, via a PCI bus, to host computer 680 for analysis and display. In some cases, the host computer may supply control signals (such as clock, synchronization and encoder signals) to the ADC and backplane components via a cable (690) connecting the host computer to the inspection tool.

The inspection tool shown in FIG. 7 presents various problems. First of all, the inspection tool fails to maximize data transfer speed, signal integrity and reliability by transferring the image data in parallel. Second, data processing is conducted by DSP boards located within the inspection tool. These boards are limited in space, power and processing capabilities. In most cases, the DSP boards lack scalability, and therefore, cannot be expanded to incorporate new features as they are developed.

A need exists for a wafer inspection system that overcomes the disadvantages mentioned above. In particular, a need exists for an improved wafer inspection system that performs a majority of the image data processing outside of the inspection tool. In addition, a need exists for an improved wafer inspection system that uses high speed serial data transfer methods to transfer image data outside of the tool.

SUMMARY OF THE INVENTION

The following description of various embodiments of a system and method is not to be construed in any way as limiting the subject matter of the appended claims.

According to one embodiment, a system is provided herein for inspecting a specimen. In general, the system may include an inspection tool for capturing images of the specimen under inspection and one or more processing nodes for processing and analyzing the inspection images. As set forth below, the processing nodes performing the image processing may be coupled to the inspection tool via one or more fibre channels. In one embodiment, the fibre channels may include an optical transmission media, such as fiber optic cables.

According to one embodiment, the inspection tool may include an illumination subsystem, a collection subsystem and a detection subsystem. The illumination subsystem may be configured for providing illumination light to the specimen, the collection subsystem may be configured for collecting light propagating from the specimen, and the detection subsystem may be configured for detecting light collected by the collection subsystem. In one embodiment, the detection subsystem may be further configured for converting the detected light into multiple channels of parallel image data. In such an embodiment, the system may be referred to as a multi-channel inspection system.

The system described herein may include many different types of inspection tools. For instance, the system may include an inspection tool configured for bright-field and/or dark-field inspection. In some embodiments, the detection subsystem may be configured for detecting the light propagating from the specimen in a line scan pattern. In other embodiments, the detection subsystem may be configured for detecting the light propagating from the specimen in a spiral pattern. Other types of inspection tools may be used, as appropriate.

In addition to the subsystems mentioned above, the inspection tool may include a data acquisition module, a bus architecture, a tool interface and a timing module. The data acquisition module is coupled to the detection subsystem for digitizing the parallel image data. The bus architecture is coupled for transferring the digital parallel image data to the tool interface in accordance with a bus protocol (e.g., a LVDS or LVPECL protocol). The timing module is coupled to the data acquisition module and the tool interface for controlling the transfer of the digital parallel image data.

The tool interface is configured to perform various data format and management functions including, but not limited to, formatting, encoding and serialization of the parallel image data. In general, the tool interface may include a receiver, a programmable element and an optical transceiver. The receiver is coupled for receiving the parallel image data from the detection subsystem and for supplying the parallel image data to the programmable element. The receiver may include any differential receiver known in the art including, but not limited to, low voltage differential signal (LVDS), low voltage positive emitter coupled logic (LVPECL) and other differential receivers having a serialized local interface.

The programmable element is coupled for receiving the parallel image data. In a preferred embodiment, the programmable element may be configured for: (i) pre-processing the parallel image data; (ii) buffering the pre-processed parallel image data until the buffered data reaches a predetermined size; (iii) forming a data packet by combining the buffered data with a data header containing information about the system; (iv) encoding the data packet; and (v) serializing the encoded data packet. In some cases, the information about the system may include one or more types of information selected from a group comprising beam position information, encoder information, processing status, packet information, channel information, pixel information and image data type. The programmable element may include substantially any programmable element capable of performing the functions mentioned above. In some cases, the programmable element may include a field programmable gate array (FPGA) or an application specific integrated circuit (ASIC).

The programmable element is configured to receive, pre-process and buffer the parallel image data at a first data rate. However, the programmable element is configured to pack, encode and serialize the data packet at a second data rate, which is much faster than the first data rate. In one embodiment, the image data may be packed, encoded and serialized in accordance with a protocol suitable for transferring information over a fibre channel. Examples of such protocols include, but are not limited to, Fibre channel (FC), serial Front Panel Data Port (sFPDP), InfiniBand and 10 Gigabit Ethernet protocols. If the sFPDP protocol is used, the image data and additional system information may be formatted into packets having a maximum size of about 2048 bytes. The data packets may then be encoded, using an 8b/10b encoding scheme or a 64b/66b encoding scheme, and serialized at data transfer rates ranging between about 1 Gbit/s to about 10 Gbit/s.

The optical transceiver is coupled to the programmable element for converting each encoded data packet into an optical signal, which is transferred serially over a single fibre channel. In most embodiments, the fibre channel preferably includes an optical transmission media, such as a fiber optic cable. Use of a fiber optic cable enables the optical signals to be transmitted over relatively long distances, ranging between a few meters to a few kilometers.

As noted above, one or more processing nodes may be included within the system for receiving and processing the optical signals transmitted serially by the tool interface. Each of the processing nodes may generally include an optical transceiver, a node interface and a processor. The optical transceiver may be coupled to one or more fibre channels for converting the optical signals received there from into electrical signals. The node interface may be coupled to the optical transceiver for deserializing and decoding the electrical signals back into individual data packets. The processor may be coupled to the node interface for processing the individual data packets to detect defects on the specimen. In some embodiments, a host computer may be included within the system for displaying the processing results. In some cases, the host computer may provide a user interface with which a user can control various inspection parameters and processing parameters.

According to another embodiment, a method for serial high-speed image data transfer in a multi-channel inspection system is contemplated herein. In some cases, the data transfer method may begin by receiving multiple channels of image data at an input data rate. As noted above, the image data may be collected from a specimen by a detection subsystem of the inspection system. Once received, the image data may be buffered at the input data rate until the buffered data reaches a predetermined size. In some cases, the input data rate may be less than or equal to about 80% of the data rate used to transfer the data over a fibre channel.

When a block of data is available, the buffered data may be packed along with a data header containing information about the system into a data packet. In some cases, the information about the system may include one or more types of information selected from a group comprising beam position information, encoder information, processing status, packet information, channel information, pixel information and image data type. Once a data packet is formed, the data packet may be encoded, serialized and converted into an optical signal. In most cases, the data will be packed, encoded and serialized at a data rate, which is much higher than the input data rate. The optical signal is transmitted over a serial fibre channel at the higher data rate to one or more processing nodes of the inspection system. The processing nodes are responsible for analyzing the optical signal to detect defects on the specimen.

In some cases, the method may include selecting the higher data rate from a group of data rates in compliance with a protocol, which is suitable for transferring information over a fibre channel. For example, the protocol may be selected from a group comprising Fiber Channel (FC), serial Front Panel Data Port (sFPDP), InfiniBand and 10G Ethernet protocols. If the sFPDP protocol is selected, the data packets may be encoded with an 8b/10b encoding scheme or a 64b/66b encoding scheme and serialized at data rates ranging between about 1 Gbit/s and about 10 Gbit/s.

BRIEF DESCRIPTION OF THE DRAWINGS

Other objects and advantages of the invention will become apparent upon reading the following detailed description and upon reference to the accompanying drawings in which.

Figure 1:
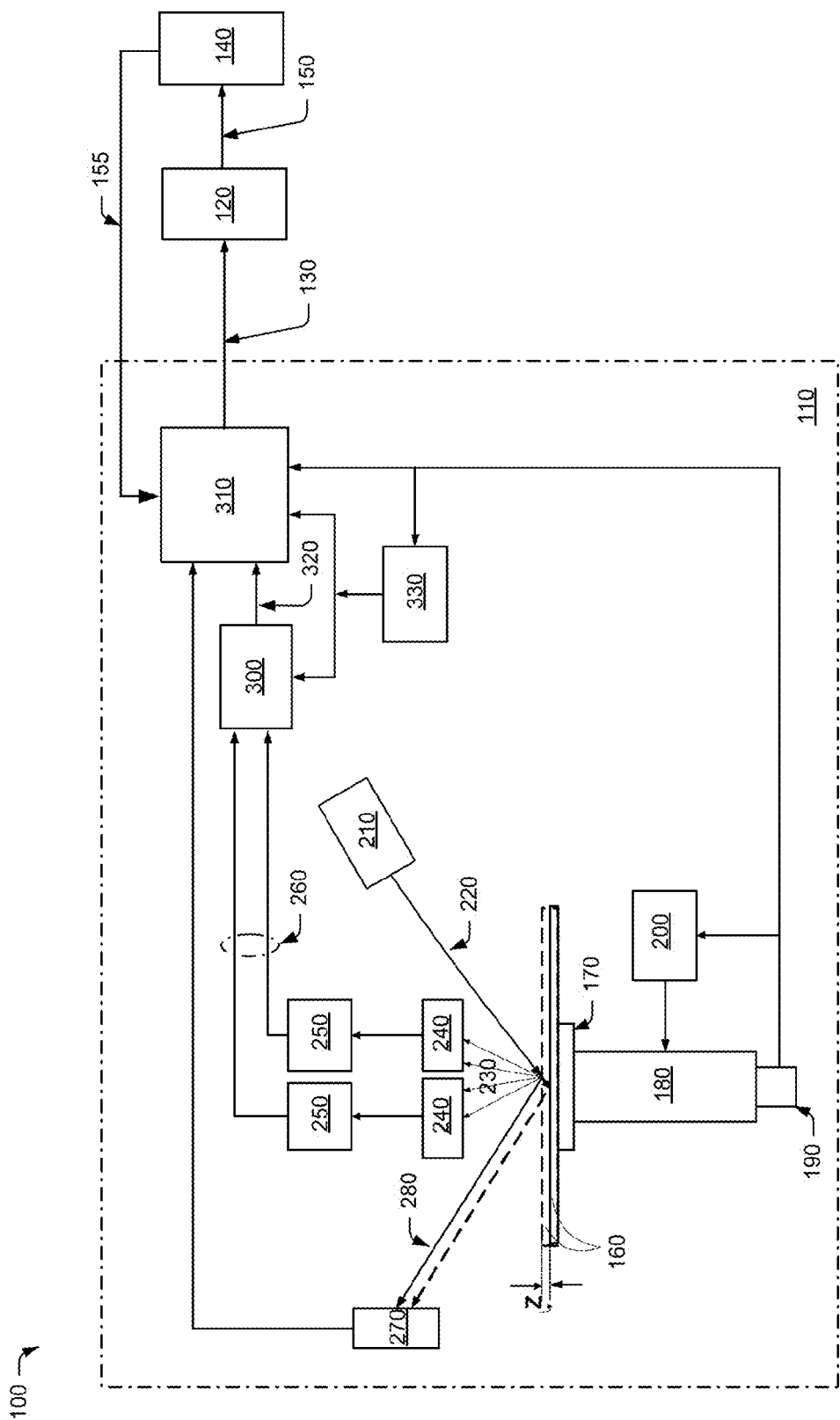
FIG. 1 is a block diagram of an inspection system, according to one embodiment of the invention.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF PREFERRED EMBODIMENTS

As used herein, the term "specimen" refers to a reticle or a wafer. The terms "reticle" and "mask" are used interchangeably herein. A reticle generally includes a transparent substrate such as glass, borosilicate glass, and fused silica having opaque regions formed thereon in a pattern. In some cases, the opaque regions may be replaced by regions etched into the transparent substrate. In some cases, the pattern may be replicated one or more times, such that a plurality of "dice" are formed on the substrate. Many different types of reticles are known in the art, and the term reticle as used herein is intended to encompass all types of reticles.

As used herein, the term "wafer" generally refers to substrates formed of a semiconductor or non-semiconductor material. Examples of a semiconductor or non-semiconductor material include, but are not limited to, monocrystalline silicon, gallium arsenide, and indium phosphide. Such substrates may be commonly found and/or processed in semiconductor fabrication facilities.

In one embodiment, the term "wafer" may refer to a bare substrate or unpatterned wafer. In another embodiment, the term "wafer" may refer to a substrate having one or more layers formed thereon. For example, such layers may include, but are not limited to, a resist, a dielectric material, and a conductive material. Many different types of such layers are known in the art, and the term "wafer" as used herein is intended to encompass a wafer including all types of such layers. The one or more layers formed on the wafer may be patterned or unpatterned. For example, a wafer may include a plurality of "dice," each having a repeatable pattern of features. Formation and processing of such layers of material may ultimately result in completed devices. Many different types of devices may be formed on a wafer, and the term "wafer" as used herein is intended to encompass a wafer on which any type of device known in the art is being fabricated.

As used herein, the term "inspection system" refers to an optical inspection system. In one embodiment, the inspection system may be a dark-field optical inspection system configured for unpatterned wafer inspection. In another embodiment, the inspection system may be bright-field inspection system configured for inspecting patterned wafers. In yet another embodiment, the inspection system described herein may combine dark-field inspection and bright-field inspection within the same tool.

In one embodiment, the inspection system described herein may comprise a line scan inspection tool, which scans an incident laser beam in the x-direction while the wafer is moved in the y-direction. The scattered light may be collected either in a large solid angle near the specular beam (for normal-incidence systems) or to the side of the wafer close to the horizon (for oblique-incidence systems). Such a tool may be used for detecting particles, pits, scratches, crystal defects and haze on bare wafers.

In a preferred embodiment, the inspection system described herein comprises a spinning scan inspection tool. In such a tool, the incident and collection optics are held stationary, while the wafer is rotated and translated beneath the optical system. The incident laser beam traverses a spiral path to sample the wafer surface. The tool may have two or more collection channels that span most, if not all of the scattering hemisphere. The collection optics are axially symmetric, allowing accurate defect capture even for defects that scatter light highly directionally, such as scratches. In addition to scratches, the spinning scan tool may be used for detecting particles, pits, crystal defects and haze on bare wafers.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

FIG. 1 illustrates an optical inspection system in accordance with one embodiment of the invention. In particular, the inspection system shown in FIG. 1 depicts a rotational or spinning scan inspection tool, which provides higher throughput than line scan tools. Although described in the context of a spinning scan inspection tool, one skilled in the art will understand how the various concepts described herein may be applied to substantially any type of inspection tool that may be used for inspecting patterned wafers, unpatterned wafers, reticles, masks or magnetic disks. The disclosure set forth below is intended to encompass all such tools.

A block diagram of an improved inspection system, according to one embodiment of the invention is shown in FIG. 1. In general, inspection system 100 includes an inspection tool or "scan tool" 110, which is connected to a number of processing nodes 120 over one or more fiber optic cables 130. Host computer 140 is connected to the processing nodes via an additional communication link 150, such as a 1G Ethernet or 10GEthernet link. In some cases, host computer 140 may be connected to inspection tool 110 for controlling various aspects of the inspection process. Control from the host to the tool can be transmitted, for example, through a Local Operating Network (LON) network interface, a USB interface, a controller area network (CAN) bus interface or a 1G Ethernet interface (155).

The inspection tool shown in FIG. 1 comprises a spinning scan tool with minimal on-board processing components. During inspection, wafer 160 is mounted on chuck 170, rotated by spindle 180, and translated by a stage (not shown) in the transverse direction. The spindle is equipped with encoder 190, which is used by motion controller 200 to provide a desired profile of rotation. Although not shown in the drawings, the stage is also equipped with an encoder, so that the motion controller may provide a desired profile of translation. The encoder information from spindle encoder 190 and the stage encoder (not shown) may be supplied to processing components of the inspection tool, as described in more detail below.

Coherent light source 210 is included within the inspection tool to provide illumination to the wafer. Light source 210 may include substantially any laser light source known in the art, examples of which include but are not limited to, continuous wave gas lasers, solid state lasers, pulsed solid state lasers, excimer gas lasers, etc. As the wafer is rotated and translated, incident laser beam 220 is scanned across the surface of the wafer in a spiral pattern. If any defects are present on the surface of the wafer, the defects will scatter light 230 that can be collected by collection optics 240, and detected by the photodetectors 250.

Collection optics 240 may include any suitable number, arrangement and/or type of optical components known in the art. In one embodiment, an imaging objective may be used to generate an optical image of the wafer as the illumination light is scanned across the surface of the specimen in the spiral pattern. As shown in FIG. 1, two or more axially symmetric collection channels may be used for collecting the scattered light over most, if not all, of the scattering hemisphere. In one embodiment (not shown), four or more collection channels may be used to improve sensitivity by collecting more scattered light. However, the inspection system described herein is not limited to a particular number of collection channels, and may include as few or as many collection channels as desired.

Photodetectors 250 convert the optical image generated by collection optics 240 into an electronic signal, which can be analyzed and displayed. In one embodiment, a pair of photomultiplier tubes (PMT) may be used to convert the optical images into electronic signals. However, photodetectors 250 are not limited to PMTs and may include substantially any number and/or type of photodetector(s) known in the art. Examples of suitable photodetectors may include, but are not limited to, time delay integration (TDI) cameras, charge-coupled device (CCD) cameras, complementary metal oxide semiconductor (CMOS) detectors and Avalanche Photodiodes.

As described in more detail below, the electrical signals from photodetectors 250 may be supplied to the processing components within tool 110 for data pre-processing and formatting. In one embodiment, the electrical signals may be supplied to acquisition electronics 300, in parallel, via high speed coaxial cables 260. The electrical signals may be supplied to the acquisition electronics at a first data rate, which is typically dictated by the inspection resolution. In one embodiment, the first data rate may be about 640 MB/s to about 2.56 GB/s. However, the first data rate is not limited to a particular data rate and may be greater, for example, if more channels are added to the inspection tool.

In some cases, the wafer thickness (Z) may vary along the radius of the wafer under inspection and/or from wafer to wafer. Variations in wafer thickness (Z) affect the position of incident laser beam 220 on the wafer, and in some cases, may result in erroneous determinations of defect locations on the wafer surface. To prevent such errors, beam position sensor 270 is included within inspection tool 110 for monitoring the light reflected from the surface of the wafer.

As the thickness of the wafer changes, reflected beam 280 moves along beam position sensor 270. This movement causes the sensor to generate a digital signal, which is proportional to the wafer thickness variation (Z). The digital signal from the beam position sensor is supplied, along with the information from spindle encoder 190 and the stage encoder (not shown), to the processing components within tool 110. Once transferred to processing nodes 120, the signals may be used as correction factors during data processing for accurately locating defects on the wafer.

As noted above, inspection tool 110 includes a number of on-board processing components. These components are typically housed within an Analog Front End (AFE) box, which includes a common backplane. As such, the on-board processing components are considered to be included within the inspection tool, itself. As set forth below, the on-board processing components may interact with one another via a network of high speed buses, which are capable of transferring information over relatively short distances (e.g., up to about 10 meters). Examples of suitable bus protocols include, but are not limited to, low voltage differential signal (LVDS), low voltage positive emitter coupled logic (LVPECL), and other protocols using a serialized local interface through the backplane.

In one embodiment, the on-board processing components may include acquisition electronics 300, tool interface 310, and timing electronics 330 (FIG. 1). The electrical signals from photodetectors 250 are digitized by analog-to-digital converters (ADCs, not shown) included within the acquisition electronics. In some cases, the acquisition electronics may convert the digital image pixels into differential signals, which can be supplied to tool interface 310 over a number of parallel buses or channels 320. Substantially any number of channels greater than 2 may be included. In one embodiment, eight (8) channels may be used for supplying the digital image pixels to tool interface 310.

In one embodiment, acquisition electronics 300 may include an LVDS transceiver (not shown) for converting the digital image pixels into LVDS signals. In such an embodiment, the LVDS signals would be transferred to tool interface 310 over parallel buses 320 in accordance with the LVDS protocol. The LVDS protocol is a differential signaling protocol, which uses a pair of wires or buses to transmit each signal (e.g., each image pixel) to a receiver. The transceiver injects a small current (e.g., about 3.5 mA) into one wire or the other, depending on the logic level (e.g., a binary "0" or "1") to be sent. The receiver determines the logic level by sensing the polarity of the voltage difference across the two wires.

The LVDS protocol is typically used to transfer information over relatively short distances, such as those found on a board or between two boards. The transmission media can be copper cables or printed circuit board (PCB) traces. The ANSI/TIA/EIA-644-A standard (published in 2001), which defines LVDS, recommends a maximum transfer distance of about 10 meters with a maximum data rate of about 655 Mbit/s (over a single twisted-pair copper wire). The LVDS protocol is desired in many applications for its relatively high speed, low noise, low cost and low power operation.

However, acquisition electronics 300 may not include an LVDS transceiver in all embodiments of the invention. One skilled in the art will understand how alternative transceivers using alternative bus protocols could be used for transferring the digital image pixels to the tool interface. Examples of alternative bus protocols include, but are not limited to, differential ECL, PECL, LVPECL, Serial ATA and TMDS. However, LVDS is currently the only bus protocol that combines low power dissipation with relatively high speed (e.g., data throughput on the order of hundreds of Mbits/s).

Timing electronics 330 is used for clocking the image pixels output from the acquisition electronics to the tool interface. In one embodiment, the timing electronics may include a phase lock loop (PLL) circuit. The PLL circuit may be configured to generate the pixel clock supplied to blocks 300 and 310 by multiplying the pulses output from spindle encoder 190. This allows the timing electronics to coordinate the image data transfer with wafer movement in the tangential direction. In addition, high resolution of acquisition is provided in the above method by making the pixel clock frequency proportional to the angular speed of spindle 180. Although not shown, timing electronics 330 may be used in some embodiments of the invention to synchronize the beam position data generated by sensor 270 to the image data generated by photodetectors 250. It is understood, however, that timing electronics 330 may not include the particular architecture and clock generation method mentioned above in all embodiments of the invention. In some cases, alternative means may be used for coordinating data transfer between the acquisition electronics, the beam position sensor and the tool interface.

Tool interface 310 is coupled for receiving the digital signals output from spindle encoder 190, translation encoder (not shown), beam position sensor 270, acquisition electronics 300, and timing electronics 330. After image signal pre-processing, the tool interface may combine the image data with the beam position information, encoder information and other system information into data packets. The packets are preferably packed, encoded and serialized in accordance with a protocol, which is suitable for transferring information over a fibre channel. After encoding and serializing the data packets, the tool interface converts the individual data packets into optical signals that can be transmitted serially over one or more fibre channels 130 to processing nodes 120. Tool interface 310 will be described in more detail below in reference to FIGS. 2-3.

Many different protocols can be used for transferring information over fibre channels 130 including, but not limited to, Fiber Channel (FC), serial Front Panel Data Port (sFPDP), InfiniBand and 10 Gigabit Ethernet. Fibre channel, in particular, is a gigabit-speed technology used for transferring information over channels or networks. The FC protocol was specifically designed to remove the barriers of performance existing in legacy networks and channels. In addition to providing scalable gigabit technology, the architects of the FC protocol provided flow control, self-management, and ultra-reliability. Fibre channel was also designed to be a transport service independent of protocol.

In a preferred embodiment, the sFPDP protocol may be used to pack, encode and serialize the data packets mentioned above. The sFPDP protocol, a subset of the Fibre Channel (FC) protocol, supports serial data transfer rates of 1.065 Gbit/s, 2.125 Gbit/s, 2.5 Gbit/s and 4.25 Gbit/s using an 8b/10b encoding scheme. A serial data transfer rate of about 10.5 Gbit/s is also provided using a 64b/66b encoding scheme. The sFPDP protocol will be described in more detail below in reference to FIGS. 2-6.

Fibre channel signals can be transmitted over both twisted pair copper wire and fiber-optic cables; however, the term "fiber" (ending in "er") always denotes an optical connection, whereas "fibre" (ending in "re") denotes a physical connection which may or may not be optical. In a preferred embodiment, fibre channels 130 mentioned above may include optical transmission media, such as one or more fiber optic cables. Unlike other transmission media, fiber optic cables provide the advantages of high speed and long distance.

Figure 4:
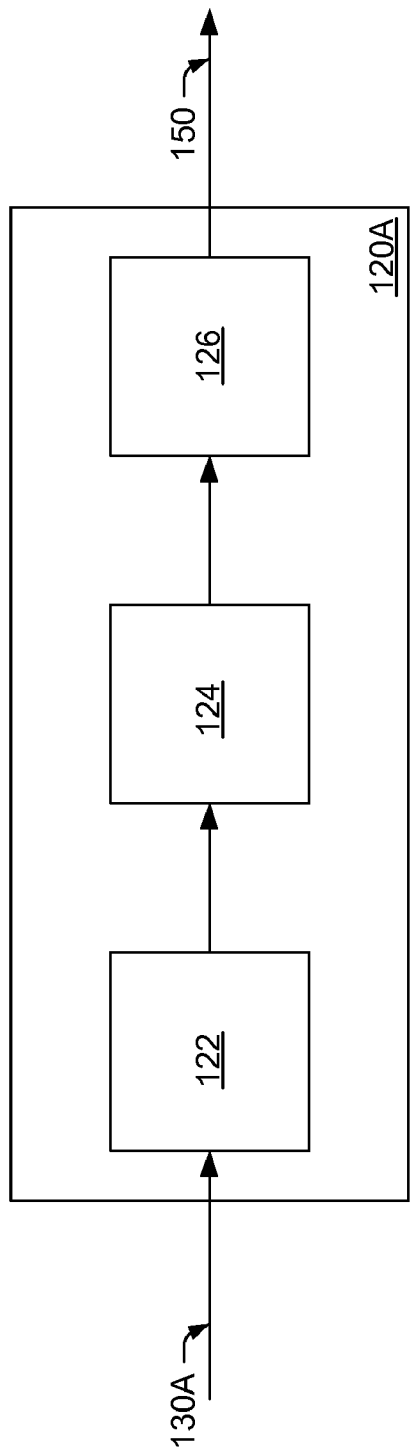
FIG. 4 is a block diagram illustrating one embodiment of a processing node included within the inspection system of FIG. 1.

Processing nodes 120 are coupled for receiving the optical signals transmitted over the fiber optic cables 130. In general and as illustrated in FIG. 4, processing node 120A may include an optical transceiver 122, which is coupled to one of the fiber optic cables 130 (e.g., 130A) for converting the optical signals received over that cable into electrical signals. In some cases, the fiber optic cables 130 may be bundled cables, each including a number (e.g., 8) of fibre channels. The electrical signals are supplied to node interface 124 for deserialization and decoding into individual data packets. Processor 126 is coupled to the node interface for processing the individual data packets, and in some cases, analyzing the imaging data.

Processing nodes 120 process the data packets to find defects, haze, etc., and produce a defect map showing locations of all detected defects. The number of processing nodes generally depends on the computational capabilities of the nodes, as well as the number of channels (e.g., 8) used for supplying image data to tool interface 310. In one embodiment, the inspection system may include four processing nodes, each implemented with a separate computer. However, the inspection system described herein is not limited to a particular number or implementation of processing nodes, and may include substantially any number/implementation deemed necessary.

If multiple nodes are present, the processing nodes may be connected in series, in parallel, or in some other configuration or topology. In one embodiment, the processing nodes may be implemented with a number of image computers connected via a known network topology. Each of the processing nodes may be configured for performing separate analysis algorithms, or different steps of the same analysis algorithm. In one embodiment, each of the processing nodes may be coupled for receiving and processing a portion of the image data. In other embodiments, the image data for an entire wafer scan may be sent to all processing nodes in parallel. In yet other embodiments, each processing node may be dedicated to a different channel for processing the image data received from that channel.

It is worth noting that the particular configuration and algorithms used to process the image data is not important and may be tailored to meet the specifications of a given application. What is important, however, is that the vast majority of data processing is performed by processing nodes located outside of inspection tool 110. Removing the processing nodes from the tool overcomes the space, power and scalability concerns that occur when internal DSP boards are used for data processing.

Host computer 190 receives the analysis results from processing nodes 120. In one embodiment, the host computer may receive the analysis results via a PCI link. However, other means may be used for connecting the host computer to the processing nodes, in other embodiments of the invention. The host computer performs various functions, such as tool calibration, displaying the analysis results, storing the analysis results and/or providing a user interface for controlling and diagnosing various aspects of the inspection or analysis process. In one embodiment, host computer 190 may supply control settings to tool interface 310 via, for example, a LON (Local Operation Network) interface.

Inspection system 100 provides many advantages over conventional systems. First of all, inspection system 100 alleviates the space, power, and scalability concerns of conventional inspection systems by performing a vast majority of the data processing outside of inspection tool 110. As noted above, one or more processing nodes 120 may be coupled to inspection tool 110 for processing the image data and locating the defects. In one embodiment, one or more fiber optic cables 130 may be used to connect the processing nodes to the inspection tool. The use of fiber optic cables enables the processing nodes to be physically separated from the inspection tool by a relatively large distance. The distance may be determined, at least in part, by the protocol used to transfer the image data to the processing nodes, and may be as little as a few meters, or as great as several kilometers. In one embodiment, the use of fiber optic cables enables the processing nodes to be located outside of the fabrication clean room, thereby saving valuable clean room space.

As another advantage, inspection system 100 alleviates signal integrity and data reliability issues by transmitting the image data to the processing nodes in a serial, rather than parallel, format. The inspection system 100 also improves data transfer speed by utilizing a high-speed fibre channel protocol, such as sFPDP, to transmit the serial image data at speeds ranging between about 1 Gbit/s and about 10 Gbit/s. Finally, inspection system 100 provides accurate defect detection by packing the image data with beam position data, encoder information and other system information. Other advantages may become apparent in light of the description provided herein.

Figure 2:
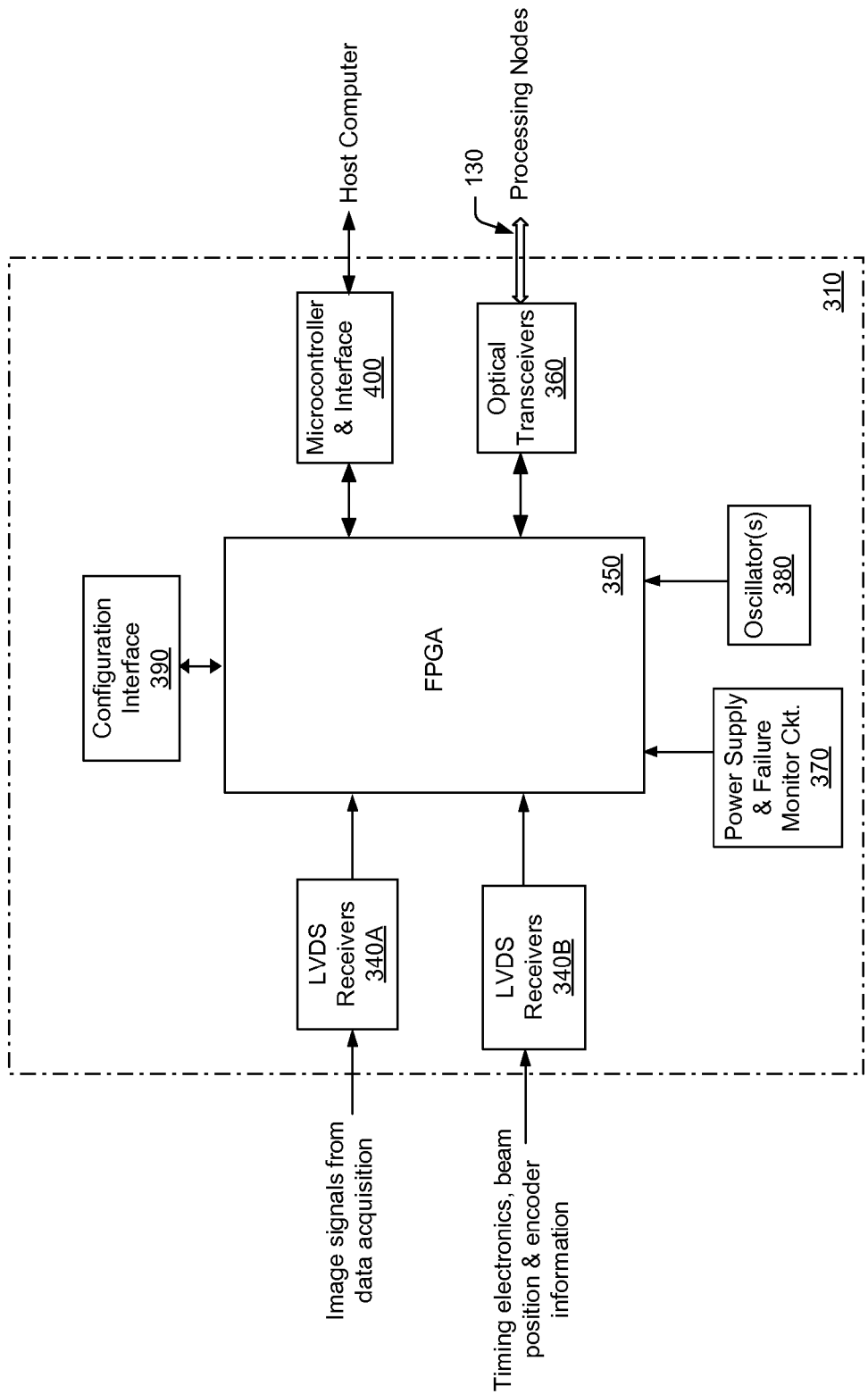
FIG. 2 is a block diagram illustrating one embodiment of the tool interface included within the inspection system of FIG. 1.

FIG. 2 is a block diagram illustrating one embodiment of tool interface 310 included within inspection system 100. As shown in FIG. 2, the tool interface may include one or more receivers 340 for receiving the digital signals supplied from spindle encoder 190, stage encoder (not shown), beam position sensor 270, acquisition electronics 300, and timing electronics 330. The LVDS receivers are also depicted in FIG. 2. One set of receivers 340A are coupled for receiving the digital image signals from acquisition electronics 300, while the other receivers 340B are coupled for receiving the pixel clock, beam position, and encoder information from the other components mentioned above. The LVDS receivers convert the LVDS signals into single-ended signals which are supplied to programmable element 350.

Figure 3:
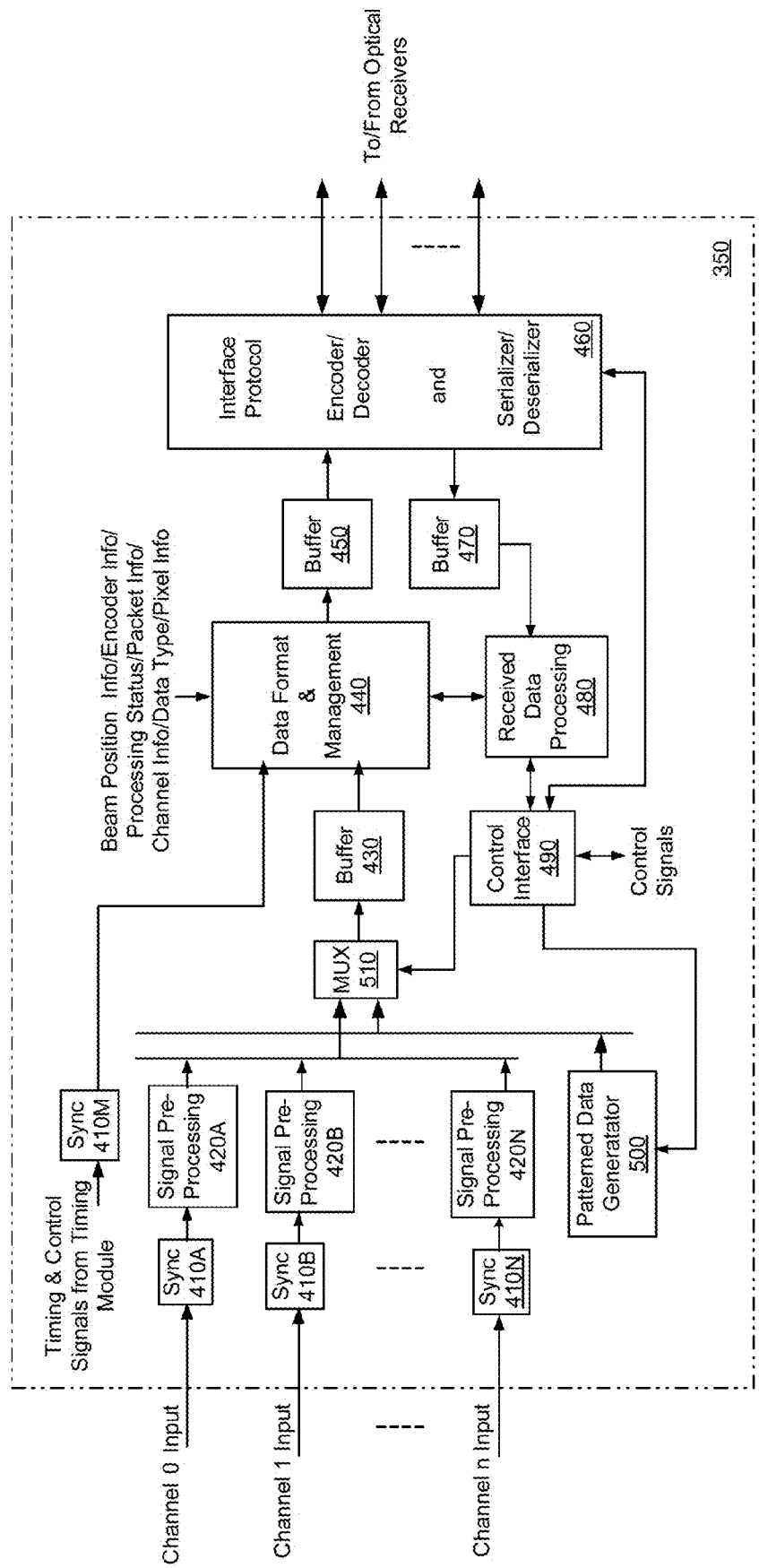
FIG. 3 is a block diagram illustrating one embodiment of the programmable element included within the tool interface of FIG. 2.

As shown in FIG. 3, the single-ended image signals from receivers 340A may be supplied to the programmable element via a number of parallel buses or channels (e.g., channels O-n). The rate at which the image signals are received by element 350 may be dictated by the ADC clock (within acquisition electronics 300), the input channel number, and the pixel clock (i.e., the clock rate used for supplying data to the tool interface). In one embodiment, the image data may be supplied to the programmable element at an input data rate, which is less than or equal to 80% of the fibre channel data rate.

Programmable element 350 may include any programmable element capable of performing the functions described herein. In one embodiment, programmable element 350 may include a field programmable gate array (FPGA) or an application specific integrated circuit (ASIC). An FPGA is illustrated in FIG. 2 and described herein, due to the fact that FPGAs are currently cheaper and more flexible than ASICs in some applications and, thus, generally more desirable. However, one skilled in the art will understand that programmable element 350 is not limited to an FPGA in all embodiments of the invention.

The primary purpose of FPGA 350 is to perform image signal pre-processing, data formatting, encoding and serialization. A functional block diagram of FPGA 350 is illustrated in FIG. 3 according to one embodiment of the invention. As shown in FIG. 3, the image data and timing signals are supplied to synchronization blocks 410. These blocks synchronize the image data and timing signals when the ADC clock (within acquisition electronics 300) differs from the pixel clock used to transfer the data to interface module 310. After synchronization, the image data undergoes pre-processing in blocks 420. Examples of pre-processing may include digital filtering, equal-distance processing, among others. However, FPGA 350 is not limited to any particular set of pre-processing algorithms. In many cases, the pre-processing capabilities of the FPGA may be modified or expanded to include additional or alternative processing algorithms.

After pre-processing is complete, the serial image data is supplied to buffer 430, where it is temporarily stored until a block of image data has been received. The buffer may be implemented with substantially any storage component known in the art, including but not limited to, First In First Out buffers (FIFOs). In one embodiment, the image data may be synchronized, pre-processed and buffered at the input data rate, or the rate at which the image data is received by tool interface 310.

Next, the buffered data is supplied to a data format and management block 440, where it is combined with additional information and formatted into data packets. In one embodiment, the additional information may include the beam position information from beam position sensor 270, as well as the encoder information from the spindle and stage encoders. As noted above, the beam position data reflects the surface height change of wafer under inspection, and may be used to calibrate the XY position of the wafer. The encoder information tracks the rotational and translational movement of the wafer under inspection, and may be used for accurate location of defects. In some cases, the additional information may also include one or more types of information, such as a current data processing status, as well as packet information (e.g., packet size), channel information (e.g., channel number or ID), pixel information (e.g., X, Z, and W pixel coordinate information, CRC error detection, auto focus data information) and image data type (e.g., edge scan data, surface scan data, microwave data, notch data, etc). If included, this type of information may be used as protocols between the tool interface and the processing nodes.

Figure 5:
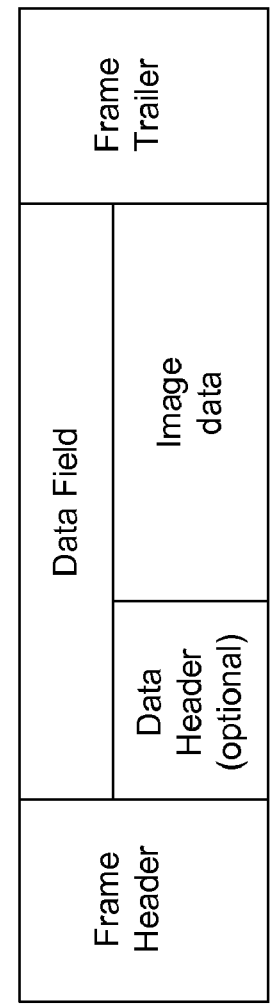
FIG. 5 is block diagram showing one manner in which image data may be formatted into a data packet.

The image data and the additional information are formatted into data packets in accordance with a protocol, which is suitable for transferring information over a fibre channel. In one embodiment, the serial Front Panel Data Port (sFPDP) protocol may be used to format the data into packets having a maximum packet size of about 2048 bytes. Each packet formatted by the sFPDP protocol may include a frame header, a frame trailer and a packet body, as shown for example in FIG. 5. In one embodiment, the frame header may include a start of frame (SOF). The frame trailer may include a trailer control field, a not ready bit, a transmit buffer overflow bit, a flow control bit, a trailer CRC and an end of frame (EOF). The packet body may include the image data and the additional information attached thereto. In the embodiment of FIG. 5, the packet payload data may include up to about 2048 bytes of image data and header information. The additional information may be attached to the payload as an optional data header.

After formatting, the data packets are buffered 450, and encoded and serialized 460 before they are transmitted out of the FPGA. In one embodiment, the data packets may be encoded and serialized in accordance with the sFPDP protocol. As indicated above, the sFPDP protocol is a subset of the fibre channel (FC) protocol, which supports serial data transfer rates of 1.065 Gbit/s, 2.125 Gbit/s, 2.5 Gbit/s and 4.25 Gbit/s using an 8b/10b encoding scheme. A serial data transfer rate of about 10.5 Gbit/s is also provided using a 64b/66b encoding scheme.

In order to provide time for data encoding and serializing, the data packets are typically formatted, encoded and serialized at a second data rate, which is much faster than the input data rate. The second data rate may include any of the sFPDP data transfer rates mentioned above. The second data rate may also include alternative data rates if, for example, a different protocol is used to format, encode and serialize the data packets. Examples of alternative protocols include, but are not limited to, Fibre Channel, InfiniBand and 10G Ethernet.

Once serialization is complete, the data packets are supplied to optical transceiver 360, where they are converted into optical signals and transferred to processing nodes 120 in series via fiber optic cables 130. In one embodiment, the fiber optic cables may be bundled cables including a number (e.g., 8) of fibre channels. Each node may use up to eight (8) fibers for transmitting and receiving, or just one fiber, depending on the processing configuration chosen. Optical transceiver 360 may include any optical transceiver design known in the art.

In some cases, the data packets received by processing nodes 120 may be fed back to the optical transceivers 360 and FPGA 350 via the fiber optic cables 130. The data fed back to the FPGA is deserialized and decoded 460, buffered 470, and supplied to a received data processing component 480. The received data may include loop back data, which can be compared to the data sent by the FPGA for diagnosis purposes, or other information received from the processing nodes.

In some embodiments, tool interface 310 may include components in addition to those already mentioned above. For example, and as shown in FIG. 2, tool interface 310 may include a power supply and failure monitor circuit 370, one or more oscillator circuits 380, a configuration interface 390, and a microcontroller and host computer interface 400. The power supply and failure monitor circuit 370 may be used for supplying power to the tool interface and for monitoring the supplied power level. Oscillator circuits 380 may be used to provide a clock to the tool interface, which is used for high speed data serialization.

Configuration interface 390 may be used by a manufacturer or end-user of the tool interface to download various codes or control settings to FPGA 350. For example, the configuration interface may be used to select the data rate (i.e., the second data rate) used to format, encode and serialize the data packets. Although other architectures may be used, configuration interface 390 may include a JTAG interface in at least one embodiment of the invention.

The microcontroller and host computer interface 400 may be used by host computer 140 to send control commands, parameters, and operation modes to the tool interface 310. In some cases, the host computer may send control signals to FPGA 350 for test and diagnosis purposes. The control signals supplied to the microcontroller and host computer interface 400 are forwarded to control interface 490 included within FPGA 350 for initiating a test sequence. Upon receiving the control signals, control interface 490 signals test pattern generator 500 to generate a test pattern. Since the test pattern can be generated and used during online tool test operation and offline test, a multiplexer (MUX) 510 is included within FPGA 350 for selectively forwarding the test pattern during test sequences. The test pattern is formatted, encoded, serialized, converted and supplied to the processing nodes, as described above for the image data. This enables the host computer to test and diagnose all components arranged within and between FPGA 350 and processing nodes 120. During normal modes of operation, the multiplexer 510 selectively forwards the image data supplied from the signal pre-processing units 420 as mentioned above.

Figure 6:
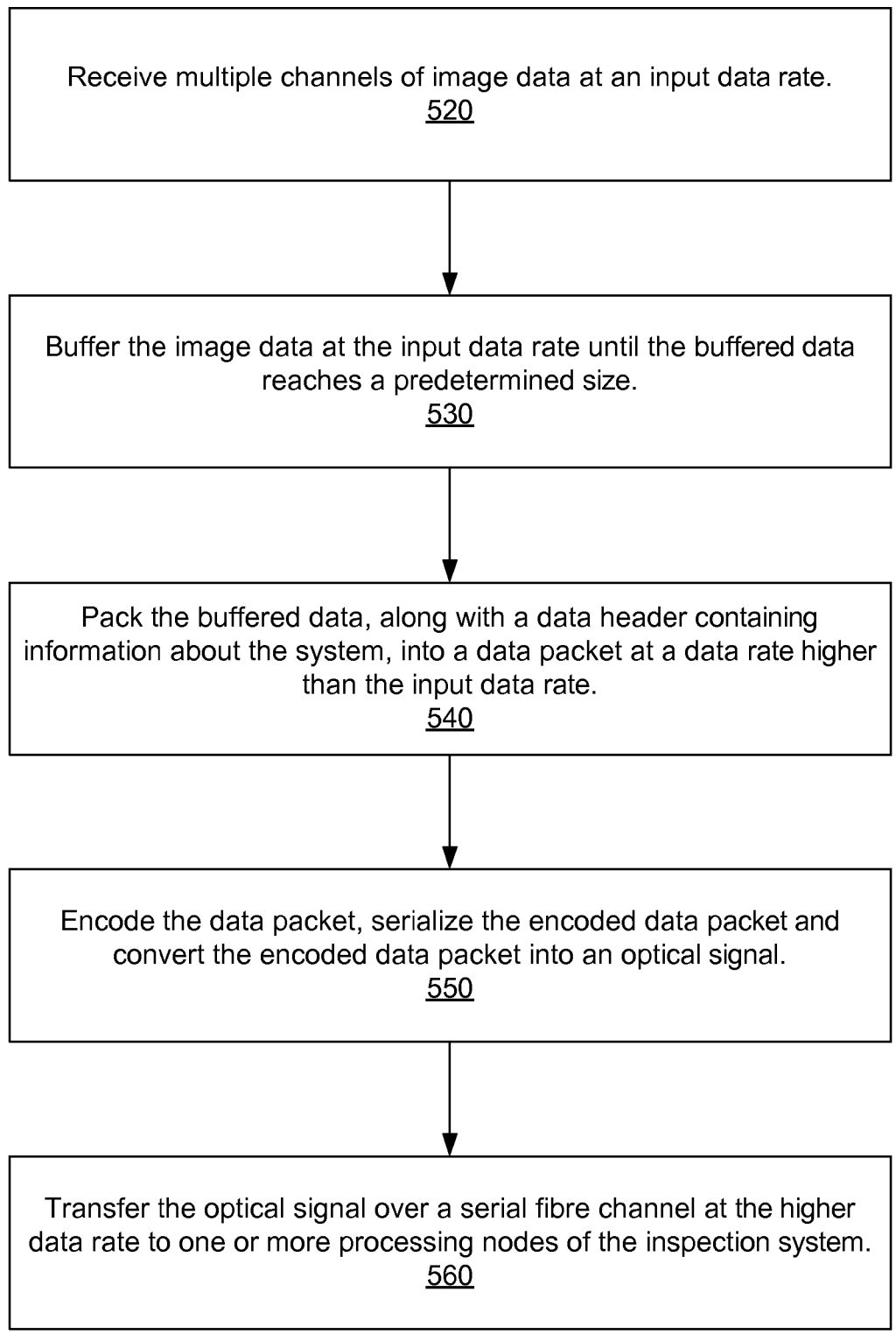
FIG. 6 is a flow chart diagram illustrating one embodiment of a method for serial high-speed image data transfer.
Figure 7:
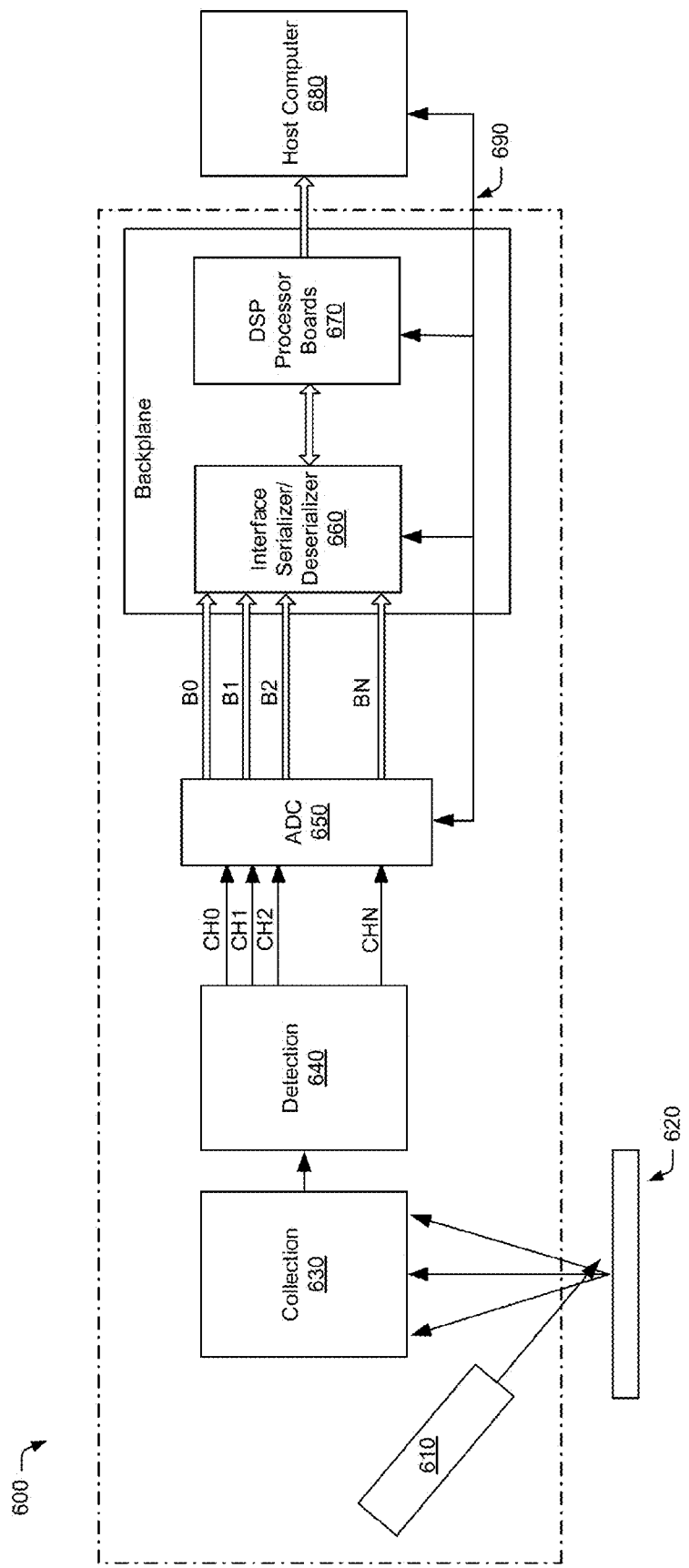
FIG. 7 is a block diagram of a conventional inspection system.

One embodiment of a method for serial high-speed image data transfer in a multi-channel inspection system is illustrated in FIG. 6. In some cases, the method may be performed by the inspection system 100 shown in FIG. 1 and described above. However, the method is not limited to the inspection tool 110 specifically shown. In some cases, other inspection tools not specifically disclosed herein may be used to generate the image data to be transferred via the method described below.

In one embodiment as illustrated in FIG. 6, the method may begin 520 by receiving multiple channels of image data at an input data rate, and buffering 530 the image data at the input data rate until the buffered data reaches a predetermined size. As noted above, the image data may be collected from a specimen (such as a wafer or reticle) by a detection subsystem of a multi-channel inspection system. The image data may be collected by any means necessary. The rate at which the image data is received (i.e., the input data rate) is typically dictated by the ADC clock, the input channel number and the pixel clock. In some cases, the input data rate may be less than or equal to about 80% of the fiber channel data rate.

Once the buffered image data reaches the predetermined size, the buffered data is packed 540 along with additional information about the system into a data packet. In some cases, the additional information may include one or more types of information selected from a group comprising beam position information, encoder information, processing status, packet information, channel information, pixel information and image data type. Other types of additional information may be included, as desired. As mentioned above, the additional information may be used, during processing steps performed after the image data is transferred, to increase the accuracy of with which defects are located on the specimen.

Once packed, the data is encoded 550, serialized, and converted into an optical signal for serial transfer 560 over one or more fiber optic cables to one or more processing nodes of the inspection system where the image signal is analyzed for detecting defects on the specimen. In most cases, the data may be packed, encoded, serialized, and converted at a data rate, which is much higher than the input data rate. In some cases, the higher data rate may be selected from a group of data rates in compliance with a protocol used for transferring information over a fibre channel. The protocol may be selected from a group of protocols comprising Fibre Channel, sFPDP, InfiniBand and 10G Ethernet. If the sFPDP protocol is selected, the data packets may be encoded with an 8b/10b or 64b/66b encoding scheme, and serialized at data rates ranging from about 1 Gbit/s and about 10 Gbit/s.

It will be appreciated to those skilled in the art having the benefit of this disclosure that this invention is believed to provide an improved wafer inspection system and method for transferring and processing inspection images. More specifically, the invention provides an inspection system 100 and method, which alleviates the space, power and scalability concerns of conventional inspection systems by performing a vast majority of the data processing outside of inspection tool 110. As noted above, processing nodes 120 are coupled to inspection tool 110 for processing the image data and locating the defects. In one embodiment, fiber optic cables 130 are used to connect the processing nodes to the inspection tool. The use of fiber optic cables is beneficial because it enables the processing nodes to be physically separated from the inspection tool by a relatively large distance (e.g., as little as a few meters, or as great as a few kilometers). In one embodiment, the use of fiber optic cables may enable the processing nodes to be located outside of the fabrication clean room, thereby saving valuable clean room space.

As another advantage, the inspection system described herein alleviates the signal integrity and data reliability concerns of conventional systems by transmitting the image data to the processing nodes in a serial, rather than parallel, format. The inspection system also improves data transfer speed by utilizing a high-speed fibre channel protocol, such as sFPDP, to transmit the serial image data at speeds ranging between about 1 Gbit/s and about 10 Gbit/s. Finally, the inspection system provides accurate defect detection by packing the image data with beam position data, encoder information and other system information.

Further modifications and alternative embodiments of various aspects of the invention will be apparent to those skilled in the art in view of this description. For example, the inspection system and method described herein use a spinning scan tool to capture the image data to be transferred and processed outside of the tool. However, the inspection system and method described herein is not limited to a spinning scan tool in all embodiments of the invention and may include substantially any other type of inspection or scan tool known in the art. It is intended, therefore, that the following claims be interpreted to embrace all such modifications and changes and, accordingly, the specification and drawings are to be regarded in an illustrative rather than a restrictive sense.

What is claimed is:

1. A system configured for inspecting a specimen, wherein the system includes an inspection tool comprising:
    a detection subsystem coupled for detecting light propagating from the specimen and converting the detected light into multiple channels of parallel image data; and
    a tool interface comprising:
        a programmable element coupled for receiving the parallel image data and configured for:
            (i) pre-processing the parallel image data;
            (ii) buffering the pre-processed parallel image data until the buffered data reaches a predetermined size;
            (iii) forming a data packet by combining the buffered data with a data header containing information about the system;
            (iv) encoding the data packet using a protocol suitable for transferring information over a fibre channel; and
            (v) serializing the encoded data packet; and
        an optical transceiver coupled to the programmable element for converting the encoded data packet into an optical signal to be transferred serially over a single fibre channel.

2. The system of claim 1, wherein the information about the system includes one or more types of information selected from a group comprising beam position information, encoder information, processing status, packet information, channel information, pixel information, and image data type.

3. The system of claim 1, wherein the protocol is selected from a group comprising Fibre Channel (FC), Serial Front Panel Data Port (SFPDP) protocol, InfiniBand, and 10G Ethernet protocols.

4. The system of claim 1, wherein the tool interface further comprises a receiver, which is coupled for receiving the parallel image data from the detection subsystem and for supplying the parallel image data to the programmable element.

5. The system of claim 4, wherein the receiver is selected from a group comprising a low voltage differential signal (LVDS) receiver, a low voltage positive emitter coupled logic (LVPECL) receiver, and other differential receivers having a serialized local interface.

6. The system of claim 4, wherein the inspection tool further comprises:
    a data acquisition module coupled to the detection subsystem for digitizing the parallel image data;
    a bus architecture coupled for transferring the digital parallel image data to the receiver in accordance with a bus protocol; and
    a timing module coupled to the data acquisition module and the tool interface for controlling the transfer of the digital parallel image data.

7. The system of claim 6, wherein the bus protocol is selected from a group comprising a low voltage differential signal (LVDS) bus protocol and a low voltage positive emitter coupled logic (LVPECL) bus protocol.

8. The system of claim 1, wherein the programmable element is configured to receive, pre-process and buffer the parallel image data at a first data rate, and wherein the programmable element is configured to form, encode, and serialize the data packet at a second data rate much faster than the first data rate.

9. The system of claim 8, wherein the second data rate is selected from a group of data rates in compliance with the Fibre Channel (FC), serial Front Panel Data Port (sFPDP), InfiniBand, and 10G Ethernet protocols.

10. The system of claim 8, wherein the programmable element is configured to encode the data packet using an 8b/10b encoding scheme or a 64b/66b encoding scheme.

11. The system of claim 1, wherein the system further comprises one or more processing nodes coupled for receiving the optical signals transmitted serially by the tool interface via the single fibre channel.

12. The system of claim 11, wherein each of the processing nodes comprise:
   an optical transceiver coupled to the single fibre channel for converting the optical signals into electrical signals;
   a node interface coupled to the optical transceiver for deserializing and decoding the electrical signals back into individual data packets; and
   a processor coupled to the node interface for processing the individual data packets to detect defects on the specimen.

13. The system of claim 11, wherein the one or more processing nodes are located a remote distance away from the inspection tool.

14. The system of claim 11, wherein the one or more processing nodes are physically separated from the inspection tool by a distance ranging between a few meters to several kilometers.

15. The system of claim 11, wherein the system further comprises a host computer coupled to the inspection tool and the processing nodes for providing a user interface with which a user can control inspection parameters, processing parameters and display inspection results.

16. The system of claim 1, wherein the system comprises a bright field inspection system.

17. The system of claim 1, wherein the system comprises a dark field inspection system.

18. The system of claim 1, wherein the system is configured for detecting the light propagating from the specimen in a spiral pattern.

19. The system of claim 1, wherein the system is configured for detecting the light propagating from the specimen in a line scan pattern.

20. A method for serial high-speed image data transfer in a multi-channel inspection system, the method comprising:
   receiving multiple channels of image data at an input data rate, wherein the image data is collected from a specimen by a detection subsystem of the inspection system;
   buffering the image data at the input data rate until the buffered data reaches a predetermined size;
   packing the buffered data, along with a data header containing information about the system, into a data packet at a data rate higher than the input data rate;
   encoding the data packet, serializing the encoded data packet and converting the encoded data packet into an optical signal; and
   transferring the optical signal over a serial fibre channel at the higher data rate to one or more processing nodes of the inspection system where the optical signal is analyzed to detect defects on the specimen.

21. The method of claim 20, wherein the input data rate is less than or equal to about 80% of the higher data rate.

22. The method of claim 20, wherein the information about the system includes one or more types of information selected from a group comprising beam position information, encoder information, processing status, packet information, channel information, pixel information and image data type.

23. The method of claim 20, further comprising selecting the higher data rate from a group of data rates in compliance with a protocol suitable for transferring information over the serial fibre channel.

24. The method of claim 23, wherein the protocol is selected from a group comprising serial Front Panel Data Port (sFPDP) protocol, Fibre Channel (FC), InfiniBand, and 10G Ethernet.

25. The method of claim 20, wherein the step of encoding comprises encoding the data packet with an 8b/10b encoding scheme or a 64b/66b encoding scheme.

* * * * *